(12) United States Patent
Lee et al.

(10) Patent No.: US 8,202,987 B2
(45) Date of Patent: Jun. 19, 2012

(54) METHOD OF OBTAINING CONFORMATIONAL POLYMORPH OF SUCROSE

(75) Inventors: Tu Lee, Flushing, NY (US); Yu-Sheng Lin, Tainan (TW)

(73) Assignee: National Central University, Taoyuan (TW)

( * ) Notice: Subject to any disclaimer, the term of this patent is extended or adjusted under 35 U.S.C. 154(b) by 0 days.

(21) Appl. No.: 12/010,310

(22) Filed: Jan. 23, 2008

(65) Prior Publication Data

US 2011/0003983 A1 Jan. 6, 2011

(30) Foreign Application Priority Data

Jun. 7, 2007 (TW) .............................. 96120495 A

(51) Int. Cl.
| | | |
|---|---|---|
| *C07H 1/00* | (2006.01) | |
| *C07H 3/00* | (2006.01) | |
| *C08B 37/00* | (2006.01) | |
| *C13K 5/00* | (2006.01) | |
| *C13K 7/00* | (2006.01) | |

(52) U.S. Cl. .................................. 536/124; 536/123.13
(58) Field of Classification Search .................. 536/124, 536/123.13
See application file for complete search history.

(56) References Cited

FOREIGN PATENT DOCUMENTS

JP 2003-319800 * 11/2003

OTHER PUBLICATIONS

Rouhi, A.M. (2003) The Right Stuff: From research and development to the clinic, getting drug crystals right is full of pitfalls. Chemical & Engineering News, vol. 81, No. 8.*
Brittain, H.G. (1999) Polymorphism in Pharmaceutical Solids—Drugs and the Pharmaceutical Sciences. Published by Marcel Dekker, Inc., New York, p. 1, 2, 178, 179, 185, 219 and 236.*
Thompson, M.D. (1999) "Chemical Development of the Drug Substance Solid Form" in Process Chemistry in the Pharmaceutical Industry. Edited by Gadamasetti, K.G., published by Marcel Dekker, Inc., p. 371-374.*
Armarego, W.L.F., Chai, C.L.L. (2003) Purification of Laboratory Chemicals. Published by Elsevier, p. 14-17, 37 and 354.*
Lee, T., Lin, Y.S. (2007) Dimorphs of sucrose. International Sugar Journal, vol. 109, No. 1303, p. 440-445.*
"Melting Range" from Minnesota State University [online], [retrieved Feb. 15, 2011]. Retrieved from the internet <http://www.mnstate.edu/jasperse/Chem355/Melting_Range.doc.pdf>.*
Dean, J.A. (1995) Analytical Chemistry Handbook. Published by McGraw-Hill, Inc., p. 10.23-10.26.*

* cited by examiner

*Primary Examiner* — Scarlett Goon
(74) *Attorney, Agent, or Firm* — Jackson IPG PLLC; Demian K. Jackson

(57) ABSTRACT

A new sucrose is obtained through the present invention. The new sucrose has a lower solubility and a lower melting point. Thus, the new sucrose has a higher stability. The new sucrose obtained through the present invention can be used as an added functionality excipient of drug in pharmaceutical industry. And the new sucrose can also be used in sugar and food industries.

1 Claim, 1 Drawing Sheet

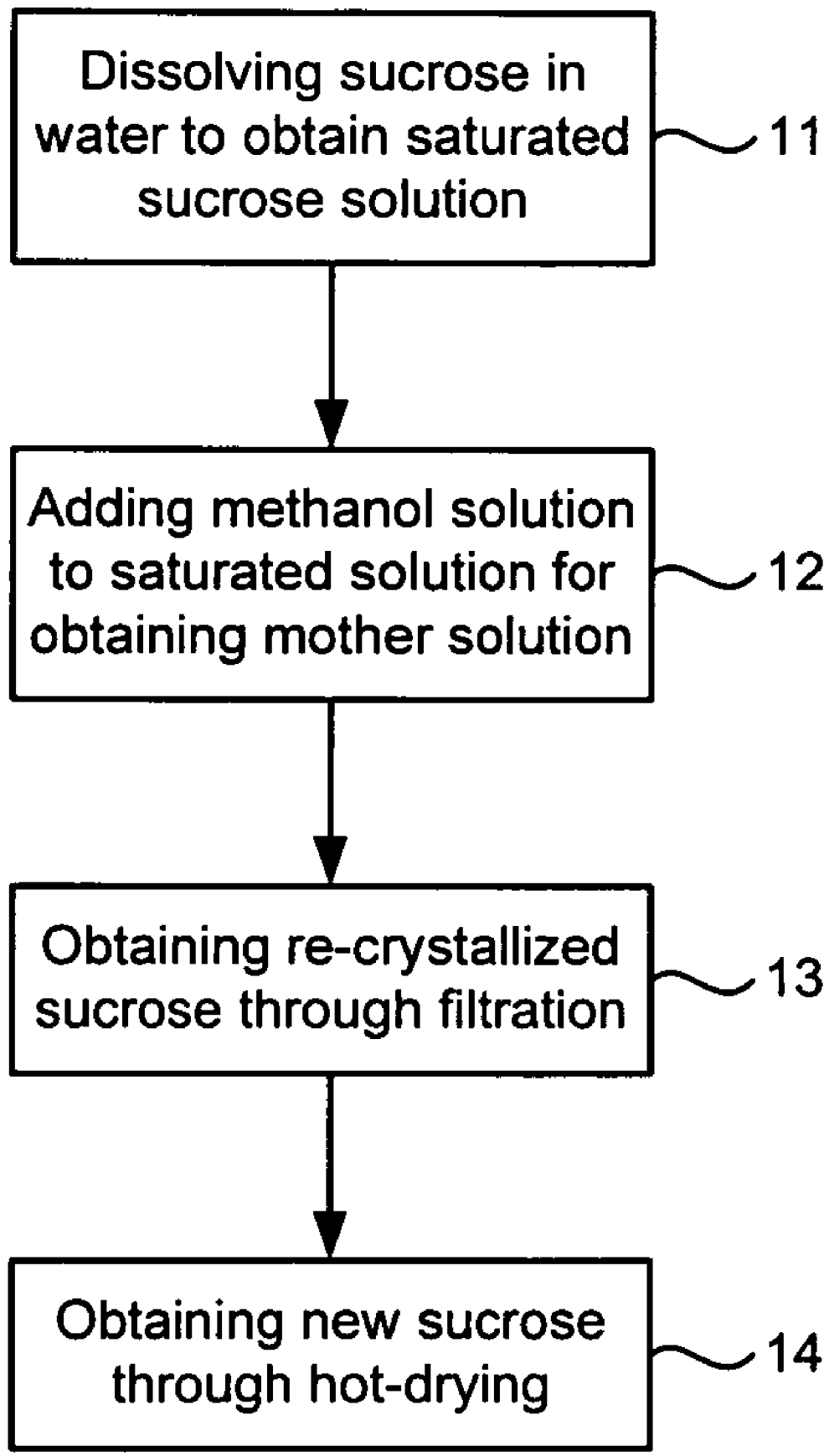

METHOD OF OBTAINING CONFORMATIONAL POLYMORPH OF SUCROSE

FIELD OF THE INVENTION

The present invention relates to obtaining a new sucrose; more particularly, relates to adding methanol to a saturated sucrose solution at 60 Celsius degrees (° C.) through an anti-solvent method for obtaining the new sucrose through re-crystallizing the saturated sucrose solution.

DESCRIPTION OF THE RELATED ART

Among sweeteners, sucrose is mass produced and has a good taste with a high stability. Thus, sucrose is suitable as additives for cooking, drinks and bakery; and, thus, is a necessity at home and even an important industrial ingredient. In addition, sucrose is a good heat source easily absorbed by human body; has abundant hydroxyl (—OH) and strong hydrophilicity; and is easily dissolved into water with an increase of solubility as the temperature is increasing. All of these advantages make sucrose a No. 1 choice among sweeteners in the market.

Only one conformational polymorph (Form I) of sucrose is found in related papers, which has a melting point between 160 and 190° C. However, sucrose has two conformational polymorphs, which are Form I and Form II. Form II conformational polymorphs can only be characterized with special analytical instruments and so only the Form I conformational polymorph (with a higher melting point of around 185 to 190° C.) is produced in the market.

Furthermore, sucrose is usually produced through evaporating a saturated solution with temperature cooling down afterwards. However, this method spends much energy. Since different conformational polymorphs exhibit different degrees of solubility, if sucrose is to be used as an added functionality excipient of drugs, the identification of the conformational polymorphs, their amounts and the control of the polymorphs in sugar quality control becomes extremely important.

SUMMARY OF THE INVENTION

The main purpose of the present invention is to add methanol to a saturated sucrose solution at 60° C. through an anti-solvent method for obtaining a new form of sucrose through re-crystallizing the saturated sucrose solution.

To achieve the above purpose, the present invention is a method of obtaining a conformational polymorph of sucrose, comprising steps of: (a) obtaining a sucrose to be totally dissolved into water and thus obtaining a saturated sucrose solution to be deposed in a temperature controlled water bath; (b) preheating methanol to be added into the saturated sucrose solution with a stirring and thus obtaining a mother solution; (c) keeping the mother solution steady to obtain a crystal and filtering the mother solution after the crystallization to obtain a re-crystallized sucrose; and (d) hot-drying the re-crystallized sucrose in a vacuum oven. Accordingly, a novel method of obtaining a conformational polymorph of sucrose is obtained.

BRIEF DESCRIPTION OF THE DRAWING

The present invention will be better understood from the following detailed description of the preferred embodiment according to the present invention, taken in conjunction with the accompanying drawing, in which FIG. 1 is the flow view showing the preferred embodiment according to the present invention.

DESCRIPTION OF THE PREFERRED EMBODIMENT

The following description of the preferred embodiment is provided to understand the features and the structures of the present invention.

Please refer to FIG. 1, which is a flow view showing a preferred embodiment according to the present invention. As shown in the FIGURE, the present invention is a method of obtaining a conformational polymorph of sucrose, comprising the following steps:

(a) Dissolving sucrose in water to obtain saturated sucrose solution 11: A 2.873 grams (g) sucrose is dissolved into 1 milliliter (ml) water and then the solution of the sucrose and water is deposed in a temperature controlled water bath at 60 Celsius degrees (° C.) for obtaining a saturated sucrose solution with the sucrose totally dissolved.

(b) Adding methanol solution to saturated solution for obtaining mother solution 12: A methanol preheated at 60° C. is mixed with water at a rate of 5:1, which comprises 5 ml methanol and 1 ml water, to be added into the saturated sucrose solution for obtaining a mother solution, where a temperature is kept at 60° C. during the whole process.

(c) Obtaining re-crystallized sucrose through filtration 13: Crystallization starts to happen in the mother solution after 4 to 5 hours (hr) of staying still. After 6 to 7 hrs, the crystallization is finished. Then, the mother liquor is filtered to obtain a re-crystallized sucrose.

(d) Obtaining new sucrose through hot-drying 14: The re-crystallized sucrose is deposed in a vacuum oven to be hot-dried at 30 to 40° C. In the end, a new form of sucrose is obtained.

Thus, a novel method of obtaining a conformational polymorph of sucrose is obtained.

On using the present invention, because sucrose has a solubility of 2873 milligrams sucrose per milliliter water at 60° C., 2.873 g sucrose is used to be dissolved into 1 ml water and the solution obtained is deposed in the temperature controlled water bath at 60° C. for obtaining the saturated sucrose solution after the sucrose is totally dissolved. Then an anti-solvent method is used at 60° C. to add methanol into the saturated sucrose solution for obtaining the new sucrose through re-crystallization. The new sucrose obtained has a melting point at 150° C., which is lower then 190° C. for the original sucrose. And the new sucrose has a higher stability than the original sucrose owing to the lower melting point. Hence, the new sucrose having the lower melting point can be used as another kind of added functionality excipient of drug, or used in cotton candy or waffle. Therefore, the present invention contributes to sugar industry, drug industry and food industry.

Through equipments like thermal analyzer, infrared spectroscopy, Karl-Fischer titrator, digital refractometer, single crystal X-ray diffractometer, nuclear magnetic resonance, variable temperature powder X-ray diffractometer etc., differences between the original sucrose and the re-crystallized sucrose are measured; and, it is found that they are obviously different in form and solubility. The re-crystallized sucrose obtained according to the present invention has a lower solubility than the original sucrose; and, the sucrose obtained according to the present invention thus has a higher stability than the original sucrose owing to the lower solubility. Conclusively, a novel conformational polymorph of sucrose is obtained according to the present invention.

To sum up, the present invention is a method of obtaining a conformational polymorph of sucrose, where a novel re-crystallized sucrose is obtained with a high stability and a low solubility to be used as an added functionality excipient of drug or used in cotton candy or waffle.

The preferred embodiment herein disclosed is not intended to unnecessarily limit the scope of the invention. Therefore, simple modifications or variations belonging to the equivalent of the scope of the claims and the instructions disclosed herein for a patent are all within the scope of the present invention.

What is claimed is:

1. A method of producing a crystalline form of sucrose having a melting point of 150° C., comprising the steps of:
    (a) dissolving sucrose in water and heating the sucrose in a temperature controlled water bath at 60° C. to obtain a saturated sucrose solution, wherein the saturated sucrose solution contains 2.873 g of sucrose per 1 mL of water;
    (b) preheating methanol to be added into said saturated sucrose solution at 60° C. with stirring and adding the preheated methanol to said saturated sucrose solution to obtain a mother liquor in a ratio of 5:1 methanol/water while maintaining the reaction at 60° C.;
    (c) keeping said mother liquor motionless to obtain a crystal and filtering said mother solution after said crystallization to obtain a re-crystallized sucrose; and
    (d) hot-drying said re-crystallized sucrose in a vacuum oven at a temperature of between 30° C. and 40° C., wherein said re-crystallized sucrose has a melting point of 150° C.

* * * * *